US010989704B2

(12) United States Patent
Asvadi et al.

(10) Patent No.: US 10,989,704 B2
(45) Date of Patent: Apr. 27, 2021

(54) SWEAT MONITORING APPARATUS AND MONITORING METHOD

(71) Applicant: KONINKLIJKE PHILIPS N.V., Eindhoven (NL)

(72) Inventors: Sima Asvadi, Eindhoven (NL); Vanda Lucia de Carvalho Vitorino de Almeida, Veldhoven (NL); Murtaza Bulut, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 440 days.

(21) Appl. No.: 15/574,303

(22) PCT Filed: Jun. 17, 2016

(86) PCT No.: PCT/EP2016/064000
§ 371 (c)(1),
(2) Date: Nov. 15, 2017

(87) PCT Pub. No.: WO2016/207070
PCT Pub. Date: Dec. 29, 2016

(65) Prior Publication Data
US 2018/0136191 A1    May 17, 2018

(30) Foreign Application Priority Data
Jun. 24, 2015   (EP) .................................. 15173671

(51) Int. Cl.
*G01N 33/487*      (2006.01)
*A61B 5/00*        (2006.01)
(Continued)

(52) U.S. Cl.
CPC ..... *G01N 33/48714* (2013.01); *A61B 5/0077* (2013.01); *A61B 5/01* (2013.01);
(Continued)

(58) Field of Classification Search
CPC ....... G01N 33/48714; G01N 33/48707; G16H 20/10; A61B 5/0077; A61B 5/01;
(Continued)

(56) References Cited

U.S. PATENT DOCUMENTS 7,831,061 B1 * 11/2010 Lubard .................. A61B 5/164
382/100
2002/0115921 A1    8/2002 Berlin
(Continued)

FOREIGN PATENT DOCUMENTS

WO         0214279 A1     2/2002

OTHER PUBLICATIONS

Larbig, "Facial thermography is a sensitive tool to determine antihistaminic activity: comparison of levocetirizine and fexofenadine", Br J Clin Pharmacol, 62:2 ,158-164 (Year: 2006).*
(Continued)

*Primary Examiner* — Regis J Betsch

(57) ABSTRACT

A monitoring apparatus for monitoring a subject (14) is disclosed. The monitoring apparatus comprises a storage device (18) for storing first skin secretion data (27) of the subject. A detection unit (12) detects a skin secretion at a skin portion of the subject and provides second skin secretion data (28) of the subject. An evaluation unit (16) evaluates the second skin secretion data and determines at least one physical parameter on the basis of the first skin secretion data and the second skin secretion data. One of the at least one physical parameter is a time value (25, 26) determinable on the basis of a difference between the first and the second skin secretion data.

12 Claims, 4 Drawing Sheets

(51) Int. Cl.
- *A61B 5/01* (2006.01)
- *G16H 20/10* (2018.01)
- *A61B 5/145* (2006.01)
- *A61B 5/1477* (2006.01)

(52) U.S. Cl.
CPC ............ *A61B 5/015* (2013.01); *A61B 5/1477* (2013.01); *A61B 5/14517* (2013.01); *A61B 5/4266* (2013.01); *G01N 33/48707* (2013.01); *G16H 20/10* (2018.01)

(58) Field of Classification Search
CPC ... A61B 5/015; A61B 5/14517; A61B 5/4266; A61B 5/1477
See application file for complete search history.

(56) References Cited

U.S. PATENT DOCUMENTS

| | | | |
|---|---|---|---|
| 2009/0204341 A1 | 8/2009 | Brauker et al. | |
| 2009/0204343 A1 | 8/2009 | Lemont, Jr. et al. | |
| 2012/0184833 A1* | 7/2012 | Kapoor | A61B 5/14521 600/346 |
| 2014/0350432 A1 | 11/2014 | Khalfallah et al. | |

OTHER PUBLICATIONS

Gamella et al., "A novel non-invasive electrochemical biosensing device for in situ determination of the alcohol content in blood by monitoring ethanolin sweat", Analytica Chimica Acta 806 (2014) 1-7 (Year: 2013).*

Larbig et al., "Facial thermography is a sensitive tool to determine antihistaminic activity: comparison of levocetirizine and fexofenadine", British Journal of Clinical Pharmacology, May 30, 2006 (Year: 2006).*

Gamella et al., "A novel non-invasive electrochemical biosensing device for in situ determination of the alcohol content in blood by monitoring ethanol in sweat", Analytica Chimica Acta 2013 (Year: 2013).*

Barnes et al., "Excretion of Methamphetamine and Amphetamine in Human Sweat Following Controlled Oral Methamphetamine Administration", Clin Chem. Jan. 2008 ; 54(1): 172-180 (Year: 2008).*

Larbig et al., "Facial thermography is a sensitive tool to determine antihistaminic activity: comparison of levocetirizine and fexofenadine", Br J Clin Pharmacol, 62:2 158-164 2006 (Year: 2006).*

Barnes, et al., "Excretion of Methamphetamine and Amphetamine in Human Sweat Following Controlled Oral Methamphetamine Administration", Drug Monitoring and Toxicology, Clinical Chemistry, 2008, 54:1, pp. 172-180.

Bandodkar, et al., "Non-invasive wearable electrochemical sensors: a review", Trends in Biotechnology, Jul. 2014, vol. 32, No. 7, pp. 363-371.

Larbig, et al., "Facial thermography is a sensitive tool to determine antihistaminic activity: comparison of levocetirizine and fexofenadine", British Journal of Clinical Pharmacology, 62:2, pp. 158-164.

Sage, et al., "Drenching sweats as an off phenomenon in parkingson's disease: Treatment and relation to plasma levodopa profile" Annals of Neurology, vol. 37, Issue 1, Jan. 1995, pp. 120-122 (Abstract).

Shibasaki, et al., "Continuous measurment of tympanic temperature with a new infrared method using an optical fiber", Journal of Applied Physiology, 1998 the American Physiological Society, pp. 921-926.

* cited by examiner

SWEAT MONITORING APPARATUS AND MONITORING METHOD

This application is the U.S. National Phase application under 35 U.S.C. § 371 of International Application No. PCT/EP2016/064000, filed on Jun. 17, 2016, which claims the benefit of European Application Serial No. 15173671.7, filed Jun. 24, 2015. These applications are hereby incorporated by reference herein.

FIELD OF THE INVENTION

The present invention relates to a monitoring apparatus for monitoring a subject on the basis of a skin secretion measurement. The present invention further relates to a monitoring method for monitoring a subject on the basis of a skin secretion measurement and in particular for assessment of vital signs information of the subject. The present invention further relates to a computer program for carrying out the steps of the method for monitoring a subject.

BACKGROUND OF THE INVENTION

In the field of monitoring of physiological conditions of a patient, it is generally known that sweat production of the patient corresponds to certain diseases and that a state of the disease can be monitored by measuring the sweat production. A corresponding system for monitoring a sweat rate of a patient by means of an electronic sensor is e.g. known from US 2002/0115921 A1.

It is further known to treat certain diseases like Parkinson's disease by the intake of drugs, wherein the dosage is usually determined and adjusted on the basis of a patient's feedback and clinical reference data and the efficiency of the medication is usually determined on the basis of patient's evaluation during a clinical visit by the patient.

It is the disadvantage of the known methods is that evaluation of the disease state is complicated and that the efficiency of the drug intake and the dosage cannot be precisely and objectively determined so that a precise medication and a precise monitoring of the progression of the disease is not possible.

SUMMARY OF THE INVENTION

It is therefore an object of the present invention to provide an improved monitoring apparatus and an improved monitoring method for monitoring a subject which provides a precise drug response monitoring and/or a precise monitoring of a disease and which is less complicated for the subject, patient or user.

In a first aspect of the present invention, a monitoring apparatus for monitoring a subject is provided comprising:
  a data storage device for storing first skin secretion data of the subject,
  a detection unit for detecting skin secretion at a skin portion of the subject and for providing second skin secretion data of the subject, and
  an evaluation unit for evaluating the second skin secretion data and for determining at least one physical parameter on the basis of the first skin secretion rate and the second skin secretion data, and
  wherein one of the at least one physical parameter is a time value determinable on the basis of a difference between the first and the second skin secretion data.

According to a further aspect of the present invention, a method for monitoring a subject is provided comprising the steps of:
  providing first skin secretion data of the subject stored in a data storage device,
  detecting skin secretion at a skin portion of the subject and providing second skin secretion data of the subject,
  evaluating the second secretion data, and
  determining at least one physical parameter on the basis of the first skin secretion data and the second skin secretion data, and wherein one of the at least one physical parameter is a time value determinable on the basis of a difference between the first and the second skin secretion data.

According to a further aspect, a computer program is provided comprising program code means for causing a computer to carry out the steps of the method according to the invention when said computer program is carried out on a computer.

Preferred embodiments of the invention are defined in the dependent claims. It shall be understood that the claim method has similar and/or identical preferred embodiments as the claimed device and as defined in the dependent claims.

The present invention is based on the idea to determine at least one physical parameter corresponding to a time dependent physiologic parameter of a subject or a patient or a user on the basis of a first stored skin secretion data of the subject and on the basis of a second measured skin secretion data of the subject in order to compare the current skin secretion data of the subject with a previously measured and stored skin secretion data of the subject so that a progression or a time dependence of a disease and/or a response to a drug intake can be objectively monitored on the basis of the skin secretion measurement. The skin secretion data may be a single value of the skin secretion or a time dependent value of the skin secretion. The first and second skin secretion data are preferably skin secretion rates. The measured skin secretion corresponds to a sweat or sebum emission of the skin. Since the skin secretion as a symptom of many diseases highly correlates with a progress of the disease or a concentration of a drug in the subject's body and the effectiveness of the drug intake and since the skin secretion can be easily measured with low effort for the subject or the user, a precise and less complicated drug response and/or disease monitor can be provided. The at least one physical parameter corresponding to a physiological parameter of the subject is preferably provided to the user or a clinical and can be considered for the adjustment of the drug medication. Since one of the measured physical parameters is a time value response time dynamics or wearing-off time dynamics of a drug intake can be determined in order to precisely determine a drug dosage individually for the subject. The time value is in particular determined as a time frame after which the difference reaches a predefined value. This is a possibility to determine a wearing-off period of a drug in the subject's body.

In a preferred embodiment, the detection unit is adapted to detect the skin secretion continuously or periodically or frequently and to provide the second skin secretion data as a time dependent skin secretion rate. This is a possibility to continuously or periodically monitor the skin secretion so that the temporal progression of the skin secretion can be considered to monitor the disease progression and/or the drug response.

In a further preferred embodiment, the at least one physical parameter is a difference between the first skin secretion data and the second skin secretion data. This is a possibility to easily determine a change of the skin secretion in order to monitor the disease progression and/or the efficiency of the drug intake.

In a further preferred embodiment, the physical parameter is a slope determinable on the basis of the difference between the first and the second skin secretion data. This is a possibility to precisely determine the increase and the decrease as time dynamics of the symptoms and the effectivity of the drugs, and hence the progression of the disease.

In a further preferred embodiment, the physical parameter is a periodic value, in particular a frequency or a cycle time determinable on the basis of the difference between the first and the second skin secretion data. This is a possibility to precisely determine the time dynamics of the symptoms and the effectiveness of the drugs.

In a further preferred embodiment, the monitoring apparatus comprises an input device for providing drug intake information of the subject to the evaluation unit, wherein the evaluation unit is adapted to determine a drug response of the subject on the basis of the at least one physical parameter. This is a possibility to directly utilize the monitoring apparatus for monitoring the drug concentration in the subject's body and the drug response of the subject.

In a further preferred embodiment, the drug intake information is a time and/or an amount of drug intake. This is a possibility to adjust the skin secretion measurement and to calibrate the measured skin secretion data to the drug medication and regimen.

In a further preferred embodiment, the monitoring apparatus comprises a temperature measuring device connected to the evaluation unit for measuring a body temperature of the subject, and wherein the evaluation unit is adapted to determine the physical parameter on the basis of the measured body temperature. This is a possibility to consider the body temperature of the subject which has a large impact on the skin secretion data, so that the preciseness of the determination of the physical parameter can be improved.

In a further preferred embodiment, the first and the second secretion data are determined on the basis of the respectively measured body temperature of the subject. This is a further possibility to further improve the detection of the first and the second secretion data.

In a further preferred embodiment, a temperature measuring device is provided for measuring an environmental temperature and wherein the at least one physical parameter is further determined on the basis of the environmental temperature. This is a possibility to improve the evaluation of the skin secretion measurement.

In a preferred embodiment, the first and the second skin secretion data is a sweat and/or sebum rate of the subject. This is a possibility to measure a body secretion of the subject which is highly responsive to a symptom of a disease and a drug efficiency so that the drug response can be monitored with high precision.

In a preferred embodiment, the detection unit comprises an infrared detector for detecting the skin secretion at the skin of the subject. This is a possibility to determine the skin secretion rate of the subject less complicated for the user and with high precision.

In a further preferred embodiment, the infrared detector is connected to the evaluation unit for measuring a body temperature of the subject. This is a possibility to determine the body temperature of the subject with low technical effort and low handling effort.

In a further preferred embodiment, the detection unit comprises an image detection unit for detecting radiation from a field of view and wherein the detection unit is adapted to determine the skin secretion at the skin portion of the subject on the basis of detected radiation. This is a possibility to detect the skin secretion rate during a long time frame e.g. overnight which is comfortable for the subject.

In a further preferred embodiment, the evaluation unit is adapted to determine a body temperature of the subject on the basis of the radiation detected by the image detection unit. This is a possibility to determine the body temperature of the subject with low technical effort and low handling effort.

In a further preferred embodiment, the evaluation unit is adapted to determine the second skin secretion rate as a skin secretion volume per area unit, wherein the evaluation unit is adapted to determine an area unit of the skin portion on the basis of image data received from the image detection unit.

In a preferred embodiment, the detection unit comprises an electrochemical sensor for detecting a concentration of at least one substance of the skin secretion, and wherein the evaluation unit is adapted to determine the physical parameter on the basis of the concentration of the at least one substance. This is a possibility to further improve the secretion detection and to improve the determination of the physical parameter, since the concentration of certain substances in the skin secretion can provide further information of the disease progression and/or the drug response of the subject.

In a further preferred embodiment, the evaluation unit is connected to a database for providing predefined skin secretion levels to the evaluation unit and wherein the evaluation unit is adapted to evaluate the second secretion data of the subject on the basis of the predefined skin secretion levels. This is a possibility to monitor the skin secretion in general, since the measured skin secretion data can be compared to usual skin secretion values so that e.g. an abnormal secretion can be identified.

In a further preferred embodiment, the first skin secretion data of the subject is reference skin secretion data of the subject measured prior to the detection of the second skin secretion data. This is a possibility to provide a reference value so that the response on drug intake and the progression of the disease can be precisely determined.

In a further preferred embodiment, the monitoring apparatus comprises an output unit for providing output information to a user on the basis of the at least one physical parameter. This is a possibility to provide the information derived from the skin secretion rate measurement to a user, e.g. a medicine so that a treatment of the subject can be installed or a medication can be adjusted.

As mentioned above, the progression of a disease or a drug response can be monitored on the basis of the measured second skin secretion data since it can be compared to the stored first skin secretion data which has been measured previously at the subject in order to provide a base line or a reference for the skin secretion measurement. Hence, a change in the skin secretion can be easily identified and the effect of a drug intake or a progression of the disease can be determined. Hence, an objective monitoring of a drug response or a disease progression can be provided with low effort for the user.

BRIEF DESCRIPTION OF THE DRAWINGS

These and other aspects of the invention will be apparent from and elucidated with reference to the embodiments described hereinafter. In the following drawings

DETAILED DESCRIPTION OF THE INVENTION

Figure 1:
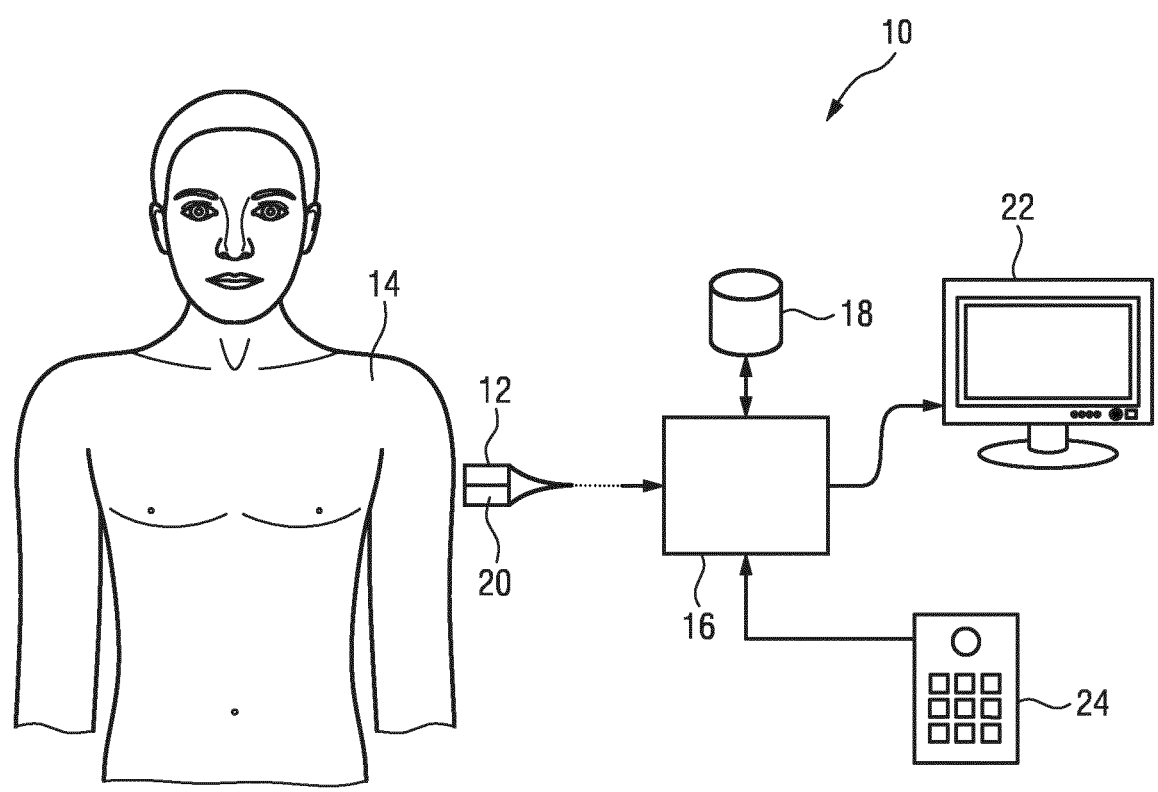
FIG. 1 shows a schematic representation of a monitoring apparatus in use to monitor a subject.

Certain embodiments will now be described in greater details with reference to the accompanying drawings. In the following description, like drawing reference numerals are used for like elements, even in different drawings. The matters defined in the description, such as detailed construction and elements, are provided to assist in a comprehensive understanding of the exemplary embodiments. Also, well-known functions or constructions are not described in detail since they would obscure the embodiments with unnecessary detail. Moreover, expressions such as "at least one of", when preceding a list of elements, modify the entire list of elements and do not modify the individual elements of the list.

FIG. 1 shows a schematic illustration of a monitoring apparatus for monitoring vital sign information of a subject, i.e. a user or a patient, wherein the monitoring apparatus is generally denoted by 10. The monitoring apparatus 10 comprises a skin secretion sensor 12 which is associated to a skin portion of a patient 14 in order to detect a skin secretion such as sweat or sebum at the skin of the patient 14. The skin secretion sensor 12 may be a contact sensor which is connectable to the skin of the patient 14 for a long time measurement and preferably formed as an infrared sensor including an infrared light source or as a skin conductivity sensor including a plurality of electrodes to provide a continuous measurement of the skin secretion provided at the surface of the skin of the patient 14. The skin secretion sensor 12 may alternatively be a contactless sensor, which is disposed separately from the patient's skin. The skin secretion sensor 12 may comprise an image detection device such as a vital sign camera which detects radiation received from the patient's skin, wherein the skin secretion is determined on the basis of detected radiation.

The monitoring apparatus 10 comprises an evaluation unit 16 as a processing unit for evaluating the skin secretion measured by the skin secretion sensor 12 and for providing skin secretion data and a corresponding result as described in the following. The evaluation unit 16 is connected to a storage device 18 to store a measured skin secretion data of the patient 14 and to provide the stored skin secretion data of the patient to the evaluation unit 17 for comparing a previously determined skin secretion data to a currently or recently measured skin secretion data. The storage device 18 may be incorporated in the evaluation unit 16 or the processing unit or may be an external storage unit or database.

The monitoring apparatus 10 further comprises a temperature measurement device 20 which is connected to the patient's body in order to measure the body temperature of the patient 14 and to provide the body temperature to the evaluation unit 16. The temperature measurement device 20 is preferably attached to or incorporated in the skin secretion sensor 12 and in a more preferred embodiment, the body temperature is determined by the infrared sensor or the image detection device of the skin secretion sensor 12 and provided to the evaluation unit 16. The monitoring apparatus 10 may further comprise a temperature measurement device for measuring the environmental temperature which can be considered during the skin secretion evaluation.

In use of the monitoring apparatus 10, a first skin secretion data is stored in the storage device 18 which has been measured in advance and which is provided as a reference value or rate to the evaluation unit 16. The skin secretion sensor 12 determines a second skin secretion data of the patient 14 and provides the second skin secretion data to the evaluation unit 16. The evaluation unit 16 evaluates the second skin secretion data and compares the second skin secretion data to the previously measured and stored first secretion data of the patient 14. The first and/or the second secretion data may be single secretion values or amounts of the skin secretion of may be time dependent amounts of secretion measured over a predefined time frame. On the basis of the difference between the first and the second skin secretion data, the evaluation unit 16 determines at least one parameter as a distinguishing feature of the first and the second skin secretion data and provides the at least one parameter which corresponds to a physiologic parameter of the patient 14 to a display unit 22 in order to provide the measurement information to a user.

The monitoring apparatus 10 further comprises an input device 24 such as a keyboard which is connected to an evaluation unit 16 in order to provide additional information or data to the evaluation unit 16.

The monitoring apparatus 10 can be used to determine a drug response of the patient 14 and the efficiency of a drug medication on the basis of the comparison of the measured second skin secretion data and the first secretion data measured e.g. without a corresponding medication. Since the skin secretion data and in particular the sweat or sebum rate of the patient 16 correspond to symptoms of certain diseases e.g. the Parkinson's disease, the efficiency of the drug medication can be determined on the basis of the detected skin secretion data. On the basis of this information, the drug dose and regimen can be adjusted in order to achieve an optimal drug concentration in the patient's body. Further, if the first skin secretion data is measured with a certain drug medication and measured during a prior state of the disease, the progression of the disease and the efficiency of the drug dose can be determined on the basis of the measured second skin secretion data. Hence, the continuous measurement of the skin secretion data compared to a previously measured skin secretion data can be utilized to determine a drug response and a progression of a disease.

The skin secretion sensor 12 may be connected to the patient's body by means of a strap or the like or may be integrated in the clothes of the patient 14 if the skin secretion sensor is based on a conductivity sensor or an infrared sensor. In a certain embodiment, the skin secretion sensor may be adapted to detect a representative compound of the skin secretion, wherein the drug response and the disease progress can be determined on the basis of the concentration of the so detected compound of the skin secretion. The first and the second skin secretion data may be based on the detection of the component of the skin secretion. One example is to detect the sodium concentration in the skin secretion.

A further embodiment of the skin secretion sensor may be based on a flexible circuit which can be attached directly to the skin and may be formed of a temporarily tattoo or the like so that lactic acid in the skin secretion can be detected.

In a preferred embodiment, the skin secretion sensor 12 and the temperature measuring device 20 are connected wirelessly to a cloud, wherein the evaluation unit 16 evaluates the measurement values stored in the cloud in order to evaluate the skin secretion data and to provide the information to the display unit 22.

Figure 2:
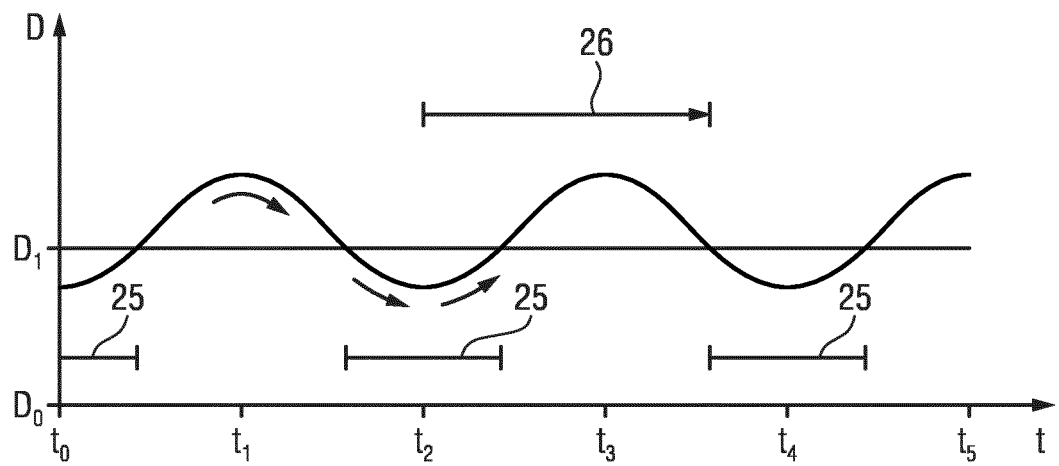
FIG. 2 shows a schematic timing diagram of a drug concentration depending on a medication frequency.

FIG. 2 shows a timing diagram of a drug concentration in the patient's body dependent on a frequent drug intake. At $t_0$, $t_2$, $t_4$, a drug is taken by the patient 14 so that the concentration of the drug in the patient's body increases after a certain response time. At $t_1$, $t_3$, $t_5$ the drug concentration reaches a maximum and after the maximum, the drug concentration is reduced again until the drug concentration reaches a minimum level at $t_2$ or $t_4$. During the increase of the drug concentration above a certain drug concentration level $D_1$, the drug starts to be effective and the symptoms of the disease are alleviated or reduced. When the drug concentration after the maximum at $t_1$, $t_3$, or $t_5$ decreases again, the symptoms of the disease begin to return. When the drug concentration in the patient's body drops below the drug concentration $D_1$, a wearing-off period of the drug is reached where the symptoms of the disease are not adequately controlled as shown at 25 in FIG. 2. A relevant parameter for the effectiveness of the medication and the dose is the time frame from the intake to the wearing-off as shown at 26. Since the skin secretion production is a certain symptom of many diseases, in particular the Parkinson's disease or cancer for lymphoma, menopause etc., the production of the skin secretion is linked to the efficiency of the drug and the corresponding dosage. Hence, the medication efficiency can be monitored on the basis of the detection of the skin secretion and on the basis of the results of the skin secretion monitoring, the medication can be adjusted or adapted. For the case of the Parkinson's disease levodopa is a preferred drug which can be monitored on the basis of the skin secretion.

Figure 3:
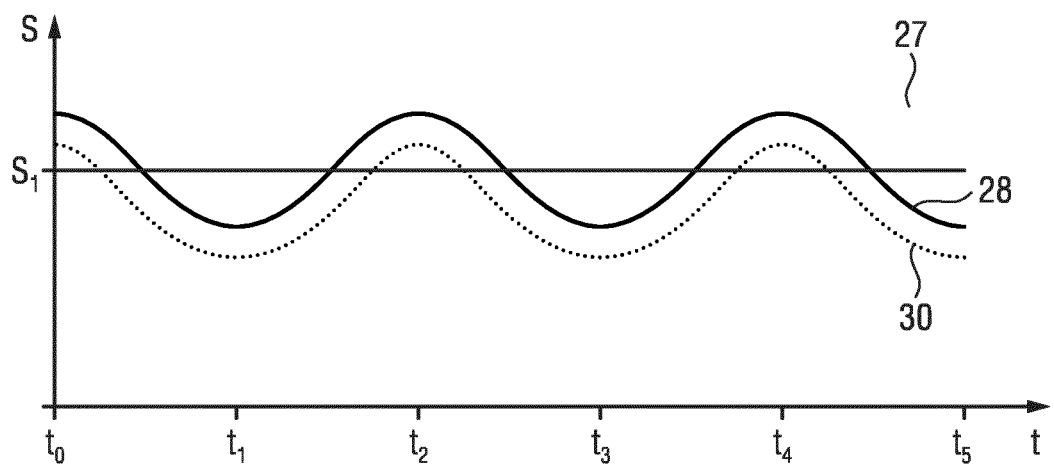
FIG. 3 shows a schematic timing diagram of different skin secretion data determined at a skin of the subject.

FIG. 3 shows a diagram of three skin secretion rates over time depending on the drug intake of the patient 14. The first skin secretion rate corresponding to the first skin secretion data, which is stored in the storage device 18 and measured previously to or in advance of the second skin secretion rate is shown as dashed line and denoted by 27. The second skin secretion rate corresponding to the first skin secretion data, which is measured by the skin secretion sensor 12 is shown as solid line and denoted by 28. The first skin secretion rate 27 is measured prior to or in advance of the drug medication or drug dosage so that the first skin secretion rate 27 is in this example constant at a high level as shown in FIG. 3. The second skin secretion rate 28 is measured after a corresponding drug intake at $t_0$ so that the second skin secretion rate 28 is reduced when the medication starts to work and the drug concentration is at a maximum level at $t_1$, $t_3$ and $t_5$. Since the first skin secretion rate 27 is usually an individual value for each person and varies over time in particular when the secretion rate is determined overnight and depends on the gender and the body temperature of the patient 14, the effectiveness of the drug dose can only be determined precisely on the basis of a difference between the first skin secretion rate 27 and the second skin secretion rate 28. By the means of the difference between the first and the second skin secretion rate 27, 28, the wearing-off of the drugs and disease progression can be precisely determined with respect to the drug intake so that a medication dose and frequency can be adjusted individual for each patient.

In order to determine the wearing-off period 25 and the time when the drugs stop to be effective can be determined on the basis of an analysis of the second skin secretion rate 28 or on the basis of an analysis of a difference between the first and the second skin secretion rate 27, 28. The time frame from the drug intake time at $t_0$, $t_2$ and $t_4$ to the time when the drug stops to be effective and/or to the wearing-off period 25 can be determined on the basis of the analysis between the first and the second skin secretion rate 27, 28 and provided as a certain time frame 26 via the display unit 22 to the user. The wearing-off period 25 can be determined as time period after which the skin secretion rate 28 or the difference between the skin secretion rates 27, 28 reaches a predefined threshold level $S_1$, which preferably corresponds to the drug concentration $D_1$. The time period may be determined as a time frame between the drug intake time and the time when the skin secretion rate 28 or the difference between the skin secretion rates 27, 28 reaches the predefined level $S_1$. Alternatively, the time period may be determined as a time frame during which the skin secretion rate 28 or the difference between the skin secretion rates 27, 28 is below the predefined threshold level $S_1$.

In a certain embodiment, the first skin secretion data can be a skin secretion rate measured during an earlier state of the disease on the influence of a certain drug as shown as dotted line in FIG. 3 and generally denoted by 30. As shown in FIG. 3, the first skin secretion rate 30 is below the second skin secretion rate 28 and indicates that the skin secretion rate has been increased with respect to the prior state of the disease so that in general the medication dose should be adjusted. Hence, the progression of the disease can be monitored by a monitoring apparatus 10 and the different skin secretion rate measurements.

The measured skin secretion rates 27, 28, 30 may be adjusted to each other on the basis of the time of the drug intake at $t_0$, $t_2$, $t_4$, which can be provided to the evaluation unit 16 by the means of the input device 24.

In a further embodiment, a slope of the measured skin secretion rates 28, 30 or of a difference between two of the skin secretion rates 27, 28, 30 may be determined in order to detect a time dynamic of the skin secretion. The slope may be determined on the basis of a continuous measurement or on the basis of certain discrete measurements and the time distance between the measurements. The slope may be determined as discrete values corresponding to two discrete measurements or as a continuous function on the basis of a derivative of the secretion function. A drug response of the patient may be determined on the basis of the slope.

In a further embodiment, a periodic value is determined on the basis of the skin secretion rate 28 or on the basis of the difference between the first 27 and the second skin secretion rate 28. The periodic value may be a frequency, a cycle time or an amplitude of the difference value.

Further personal or environmental factors which may influence the skin secretion measurements can be provided to the evaluation unit 16 via the input device 24 and which may be utilized to adapt the respective skin secretion data measurement. The influence factors are for example exercise, movement, food, environmental temperature, physiological state, core body temperature, hormones, gender related differences and the medication.

The measured skin secretion rate 28 may also be evaluated with respect to normal secretion production threshold levels which are e.g. known from the literature so that the skin secretion such as sweat and sebum production can be quantitatively evaluated and used to provide the right dosage of the drugs.

The information derived from the different secretion data determined by the evaluation unit 16 is provided by the display unit 22 and used by the clinician to assess a state of the patient and to provide a personalized care.

Figure 4:
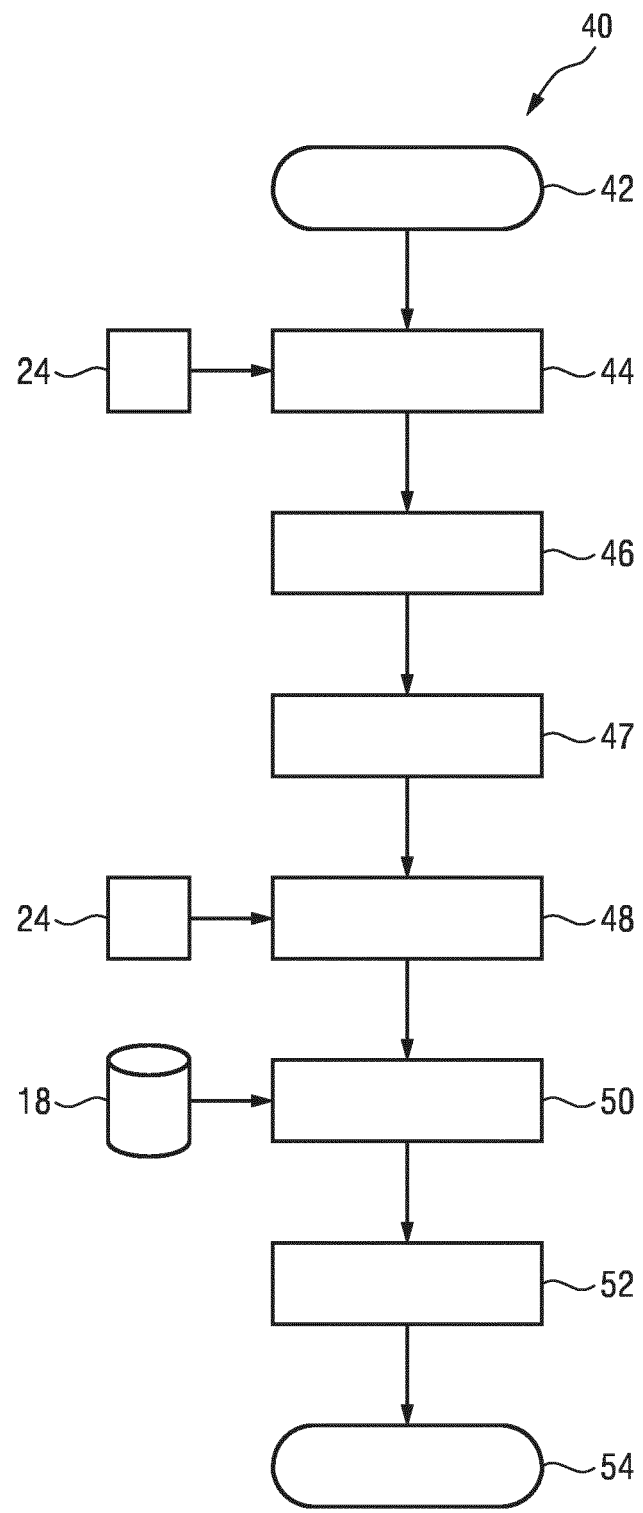
FIG. 4 shows a schematic flow diagram of a monitoring method for monitoring a subject.

In FIG. 4, a schematic flow diagram of a monitoring method is schematically shown and generally denoted by 40. The monitoring method 40 starts at step 42, wherein at step 44 the skin secretion of the patient 14 and in particular the body temperature of the patient 14 are measured e.g. by the sensors 12, 20. On the basis of these measurements, the first secretion data 27 is determined or calculated as a reference and stored in the storage device 18 as shown at step 44. Additional information may be utilized for the calculation of the first secretion data 27 and provided via the input device 24.

At step 46 a drug is taken by the patient 14 and the intake information is provided to the evaluation unit 16 via the input device 24. At step 47, the skin secretion of the patient 14 is measured continuously or frequently by the skin secretion sensor 12 and in particular the body temperature is measured by means of the temperature measuring device 20. At step 48, the second skin secretion data 28 is evaluated on the basis of the skin secretion measurement and on the basis of additional information like exercise, movement, food, environmental temperature, physiological state, core body temperature, hormones, gender related differences and the medication and e.g. provided by means of the input device 24. At step 50, the stored first skin secretion data 27 and the last measured second skin secretion data 28 are compared and the relevant parameter 25, 26 corresponding to a drug response or a disease progress are derived from the difference of these skin secretion data.

At step 52, the relevant information is provided to the user via the display unit 22 on the basis of the determined parameter so that the user can assess the state of the patient and introduce an individual medication and a personalized care.

At step 54, the monitoring method 40 ends.

Figure 5:
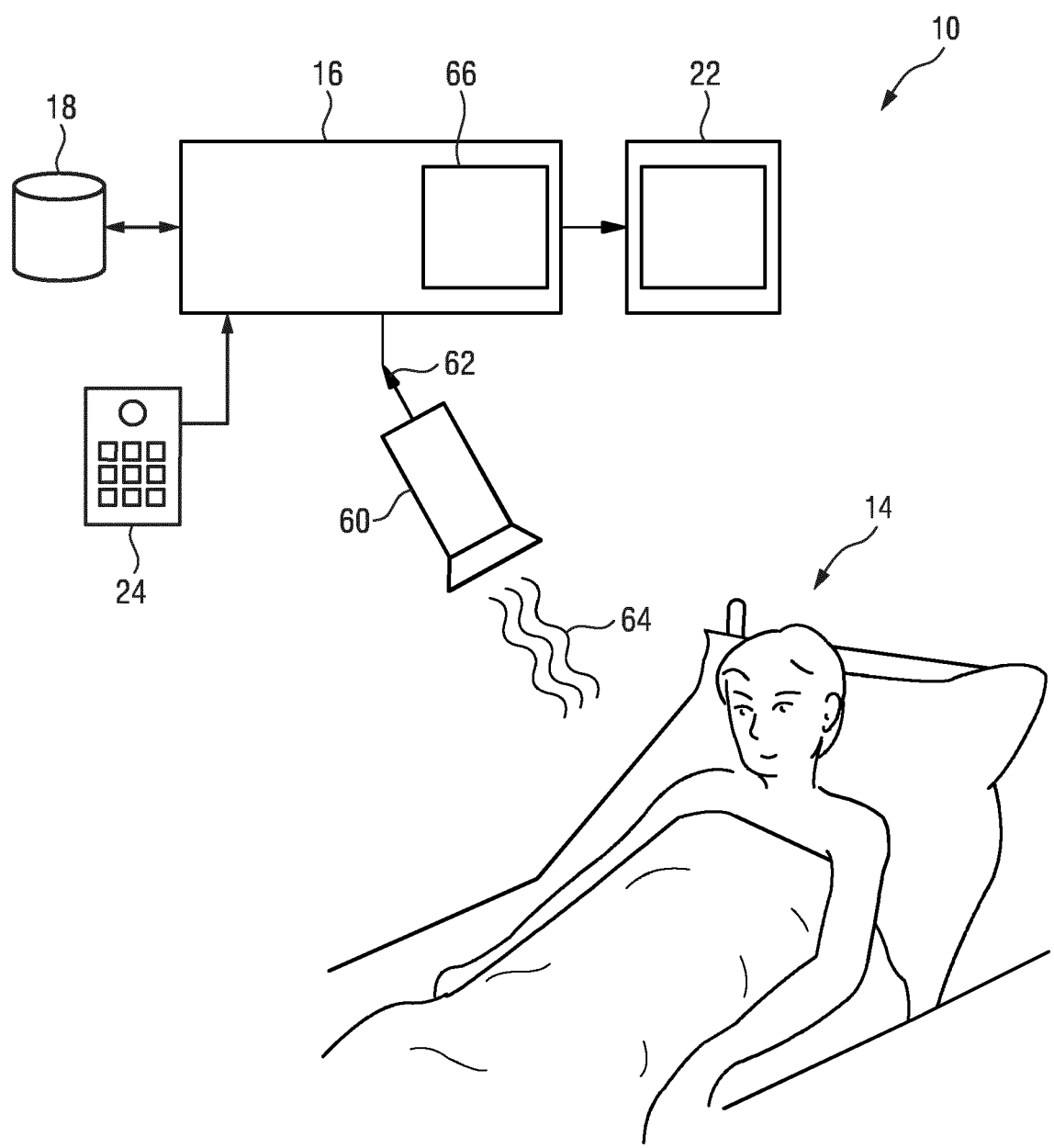
FIG. 5 shows an embodiment of the monitoring apparatus including an image detection device to monitor the subject.

FIG. 5 shows an alternative embodiment of the monitoring apparatus 10 including a detection unit for detecting the skin secretion information of the patient 14 contactless.

The monitoring apparatus 10 comprises for detecting the skin secretion rate of the patient 14 an image detection device 60, e.g. a monochromatic camera which can be used for capturing and recording image frames of the patient 14 and for providing image data 62 to the evaluation unit 16. The image frames can be derived from electromagnetic radiation 64 emitted or reflected by the patient's skin. For extracting image information from the image data 62, e.g. a sequence of image frames, the image data 62 is provided to the evaluation unit 16 which includes an image processing unit 66 for image processing.

The image detection device 60 is adapted to capture images belonging to at least a spectral component of the electromagnetic radiation 64 and preferably a spectral component of the infrared spectrum of the electromagnetic radiation 64. The image detection device 60 may provide single images, continuous image data or a discrete sequence of image frames captured from a field of view including the patient 14 to be measured.

The image processing unit 66 is adapted to evaluate the image data 26 in general and to determine the skin secretion on the basis of the reflected electromagnetic radiation 64, in particular the reflected infrared radiation.

The evaluation unit 16 may also determine the body temperature of the patient 14 on the basis of the detected radiation 64 and to utilize the body temperature to evaluate the detected skin secretion rate. Further relevant influence factors may be determined by the evaluation unit 16 and the image detection device 60 on the basis of the detected radiation 64 like exercise, movement of the patient 14, or environmental temperature.

The evaluation unit 16 may also determine the skin secretion rate 28 as a skin secretion volume per area unit, wherein the area unit is determined as a skin portion of the patient 14 on the basis of the image data 62 received from the image detection device 60.

By means of this embodiment of the monitoring apparatus 10, the patient 14 can be monitored contactless over a long time frame e.g. staying in bed overnight which is highly comfortable for the patient 14.

In an example of the invention, it is provided a monitoring apparatus for monitoring a subject, comprising: i) a data storage device for storing first skin secretion data of the subject, ii) a detection unit for detecting a skin secretion at a skin portion of the subject and for providing second skin secretion data of the subject, and iii) an evaluation unit for evaluating the second skin secretion data and for determining at least one physical parameter on the basis of the first skin secretion data and the second skin secretion data.

In a further example of the invention, a corresponding method is also provided, method for monitoring a subject, comprising the steps of: i) providing first skin secretion data of the subject stored in a data storage device, ii) detecting skin secretion at a skin portion of the subject and providing second skin secretion data of the subject, iii) evaluating the second skin secretion data, and iv) determining at least one physical parameter on the basis of the first skin secretion data and the second skin secretion data.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A monitoring apparatus adapted to monitor a subject, comprising:
   a data storage device configured to store first skin secretion data of the subject, wherein the first skin secretion data is from the subject;
   a detection unit configured to
      detect a skin secretion at a skin portion of the subject and
      detect, with an image detection device, radiation from a field of view,
      determine the skin secretion at the skin portion of the subject based on the detected radiation, and provide second skin secretion data of the subject;
an evaluation unit configured to evaluate the second skin secretion data; and
a temperature measuring device, connected to the evaluation unit, configured to measure a body temperature of the subject, wherein the evaluation unit is further configured to determine at least one physical parameter based upon the measured body temperature, the first skin secretion data, and the second skin secretion data, and the at least one physical parameter is a time value determinable based upon a difference between the first skin secretion data and the second skin secretion data.

2. The monitoring apparatus as claimed in claim 1, wherein the detection unit is further configured to
detect the skin secretion continuously or periodically and provide the second skin secretion data as a time dependent skin secretion rate.

3. The monitoring apparatus as claimed in claim 1, wherein the at least one physical parameter is a difference determinable between the first skin secretion data and the second skin secretion data.

4. The monitoring apparatus as claimed in claim 1, wherein the at least one physical parameter is a slope determinable based upon the difference between the first skin secretion data and the second skin secretion data.

5. The monitoring apparatus as claimed in claim 1, further comprising:
an input device configured to provide drug intake information of the subject to the evaluation unit, wherein the evaluation unit is further configured to determine a drug response of the subject based upon the at least one physical parameter.

6. The monitoring apparatus as claimed in claim 1, wherein the first skin secretion data and the second skin secretion data are sweat and/or sebum rates of the subject.

7. The monitoring apparatus as claimed in claim 1, wherein the detection unit further comprises:
an electrochemical sensor configured to detect a concentration of at least one substance of the skin secretion, wherein the evaluation unit is further configured to determine the at least one physical parameter based upon the concentration of the at least one substance.

8. The monitoring apparatus as claimed in claim 1, wherein the evaluation unit is connected to a database for providing skin secretion levels to the evaluation unit and wherein the evaluation unit is further configured to evaluate the second skin secretion data of the subject based upon the skin secretion levels.

9. The monitoring apparatus as claimed in claim 1, wherein the first skin secretion data of the subject forms reference skin secretion data of the subject measured prior to the detection of the second skin secretion data.

10. The monitoring apparatus as claimed in claim 1, further comprising:
an output unit configured to provide output information to a user based upon the at least one physical parameter.

11. A method for monitoring a subject, the method comprising:
providing first skin secretion data of the subject stored in a data storage device, wherein the first skin secretion data is from the subject;
detecting a skin secretion at a skin portion of the subject; and
detecting, with an image detection device, radiation from a field of view;
determining the skin secretion at the skin portion of the subject based on the detected radiation;
providing second skin secretion data of the subject;
evaluating the second skin secretion data;
measuring, with a temperature measuring device, a body temperature of the subject; and
determining at least one physical parameter based upon the measured body temperature, the first skin secretion data, and the second skin secretion data, wherein the at least one physical parameter is a time value determinable based upon a difference between the first skin secretion data and the second skin secretion data.

12. A non-transitory computer-readable medium comprising instructions that are executed on a computer to carry out a method for monitoring a subject, the non-transitory computer-readable medium comprising:
instructions for providing first skin secretion data of the subject stored in a data storage device, wherein the first skin secretion data is from the subject;
instructions for detecting a skin secretion at a skin portion of the subject;
instructions for detecting, with an image detection device, radiation from a field of view;
instructions for determining the skin secretion at the skin portion of the subject based on the detected radiation;
instructions for providing second skin secretion data of the subject;
instructions for evaluating the second skin secretion data;
instructions for measuring, with a temperature measuring device, a body temperature of the subject; and
instructions for determining at least one physical parameter based upon the measured body temperature, the first skin secretion data, and the second skin secretion data, wherein the at least one physical parameter is a time value determinable based upon a difference between the first skin secretion data and the second skin secretion data.

* * * * *